United States Patent [19]

Telfer et al.

[11] Patent Number: 4,890,484
[45] Date of Patent: Jan. 2, 1990

[54] AUTOMATED METHOD AND APPARATUS FOR DETERMINING TOTAL SUSPENDED SOLIDS IN LIQUIDS

[75] Inventors: Alexander Telfer; Joseph C. Raia, both of Houston, Tex.

[73] Assignee: Shell Oil Company, Houston, Tex.

[21] Appl. No.: 149,317

[22] Filed: Jan. 28, 1988

[51] Int. Cl.⁴ .................................................. G01N 1/10
[52] U.S. Cl. ................................. 73/61 R; 73/863.01
[58] Field of Search ............... 73/61 R, 61.4, 863.01, 73/863.23; 162/49, 198, 263; 210/143

[56] References Cited

U.S. PATENT DOCUMENTS 3,893,333  7/1975  Sunahara et al. ................... 73/61 R
4,704,899  11/1987 Burr et al. ........................... 73/61 R Primary Examiner—Hazron E. Williams

[57] ABSTRACT

The determination of total suspended solids (non-filterable residue) in water and waste water is automated to operate without operator intervention. Volatile total suspended solids can also be determined.

18 Claims, 3 Drawing Sheets

AUTOMATED METHOD AND APPARATUS FOR DETERMINING TOTAL SUSPENDED SOLIDS IN LIQUIDS

BACKGROUND OF THE INVENTION

The present invention relates to robotics systems for use in automated laboratory applications, and more particularly to a method and apparatus for the automated determination of total suspended solids (non-filterable residue) in water and waste water.

Automation in analytical laboratories is not, of itself, a new concept, but instead has been widely practiced for many years. More recently, it has appeared mainly in the form of microprocessor controlled analytical instrumentation with dedicated hardware, such as auto samplers, continuous flow systems, and computerized data collection, calculation, and report generation facilities. The very recent past has seen important improvements wherein laboratory automation has been extended by the use of robotics, combined with programmable computers, to new tasks which include sample preparation, and even entire analytical determinations. The first such robotic system was introduced in 1982 by Zymark Corporation (Hopkinton, Mass.). As experience has been gained with these systems, they have been successfully applied to ever more sophisticated laboratory operations.

An example has to do with the filtration of liquids, and in particular the filtration of a sample through an extremely fine filter for measuring suspended solids. Environmental Protection Agency requirements, such as in the EPA approved protocol specified in the manual procedure US EPA method 160.2 for the determination of total suspended solids (TSS) in water and waste water is routinely performed at many manufacturing locations throughout the country, and in support of waste water treatment research and development studies. It is a routine EPA test procedure that is highly repetitive, usually involves a large number of samples to be analyzed, and requires the committed attention of the human analyst—a prime example of a procedure wherein robotic automation would be highly desirable.

Although the repetitive nature of the procedure and the large number of sample analyses typically performed made the total suspended solids analysis a good candidate for automation, it was discovered that such a robotic procedure involved a much more complex system than commercially available. Although the procedure involved sample preparation steps which had already been successfully performed by other laboratory robotic systems, it also included operations that required robot-friendly modules and sensors, and procedures for their exploitation, which were not yet commercially available. In other words, while the procedure was well established for manual execution by a human operator, its automation in a robotics environment was found to be beyond the state of the robotics art.

A need therefore remains for an automated method and apparatus for determining total suspended solids in liquids, and particularly for such a method which can be implemented on a robotics system in a robot-friendly manner in order to substantially eliminate the performance of the repetitive steps by hand. Such a method should be highly accurate, efficient, reliable, repeatable, non-intrusive, non-invasive (to prevent contamination), and sufficiently economical to lend itself to widespread utilization in such analyses.

SUMMARY OF THE INVENTION

Briefly, the present invention meets the above needs and purposes with a new and improved automated method and apparatus for determining total suspended solids in liquids. The liquid samples are contained in sample flasks and are filtered through crucibles which support filters therein on their perforated bases.

In operation, the robotics system robot arm and manipulator first gets a fresh, dry crucible with a filter therein from the system's desiccator and moves the crucible to the system's balance where the initial or tare weight is obtained. Next, the robot takes the crucible and filter to the system's rinse station where a small quantity (2-ml) of water is placed on the filter. This helps seal the filter to the crucible. The robot then places them into the system's filter station, and backs away. Vacuum in the filter station is applied to the base of the crucible, and a capacitance electronics system in the filter station takes a reading of the initial or base capacitance of the crucible and filter.

Next, the robot gets a sample flask from the system's storage rack and inverts the flask into the crucible. The robot leaves the flask in a holder at the top of the filter station, with the neck of the flask below the top of the crucible. This allows up to 100 m/l of sample to be filtered using a crucible of only about 40 m/l capacity. The crucible will not overflow since the neck of the flask is sealed below the liquid surface. The robot backs away and a second capacitance measurement is made. If the filtration is complete, this second reading will approach the base reading, and the vacuum will be shut off for that filter station. If not, the robot proceeds with loading the next sample and rechecks all loaded stations until filtration is complete. The rinse procedure operates in exactly the same way. The samples can sit for some time without affecting the performance as long as the vacuum is off. Preferably, the filters are not allowed to dry. Similarly, the filters should not be too wet prior to placing them in the oven. For this reason, just before the filter-containing crucibles are loaded into the oven the vacuum is again briefly applied to remove any accumulated droplets.

Next, the crucibles are heated in the system's oven at 105° C. for two hours to remove moisture, then cooled in the system's desiccator and subsequently re-weighed. This provides a final weight, which is verified by again heating, cooling, and weighing the crucible as before. The amount of suspended solids then removed by the filter is determined by calculating the difference between the initial and final weights.

It is therefore an object of the present invention to provide a new and improved method and apparatus for the automated determination of total suspended solids in liquids; such a method and apparatus which can be directly and readily implemented by means of an automated robotic manipulator; in which the automated procedure is commenced by weighing a fresh, dry, filter-containing vessel to determine its initial weight; in which the automated robotic manipulator then places the vessel in the system's filtration station; in which the manipulator then inverts a sample-containing sample vessel in the filtration station over the filter-containing vessel; which continues by detecting conclusion of the filtration of the liquid sample through the filter-containing vessel in the filtration station; which next adds clean rinse liquid to the drained sample vessel; which then again inverts the sample vessel in the filtration station over the filter-containing vessel to pour residual sample solids from the sample vessel into the filter-containing vessel; which then again detects conclusion of the filtration of the liquid through the filter-containing vessel in the filtration station; in which the filter-containing vessel is then heated to dry it; in which the filter-containing vessel is then cooled in the system's desiccator; in which the filter-containing vessel is then re-weighed; in which the difference between the initial and final weights is then calculated to determine the weight of the suspended solids removed by the filter from the liquid sample; in which the filter-containing vessel may be a crucible; in which the fresh, dry, filter-containing vessel may be stored in the system's desiccator prior to weighing the dry vessel to determine it's initial weight; in which the filter in the filter-containing vessel may be moistened prior to inverting the sample-containing vessel over the filter-containing vessel in the filtration station; in which the sample-containing sample vessel may be a flask; in which the sample-containing sample vessel may be initially stored in a storage rack and finally returned thereto when empty; in which the rinsing steps may be repeated several times to improve removal of residual sample solids from the sample vessel and to wash the filter cake; in which a vacuum may be applied to the filter-containing vessel to expedite filtration of the liquid sample through the filter; in which such a vacuum may be re-applied to the filter-containing vessel just prior to the removal thereof from the system's filtration station; in which the heating, cooling, and re-weighing steps may be repeated to verify the final weight; in which volatile suspended solids may also be determined by heating the filter-containing vessel in a furnace to vaporize the volatile suspended solids in the filtrate, cooling the filter-containing vessel, and again weighing the vessel, and based on the weights determined in the several weighing and re-weighing steps, calculating volatile total suspended solids as well as the total of all suspended solids removed by the filter from the liquid sample; and to accomplish the above objects and purposes in an inexpensive, uncomplicated, durable, versatile, and reliable method and apparatus, inexpensive to implement, and widely suited to the widest possible utilization in robot-friendly applications for determining total suspended solids in liquid samples.

These and other objects and advantages of the invention will be apparent from the following description, the accompanying drawings, and the appended claims.

DESCRIPTION OF THE PREFERRED EMBODIMENTS

Figure 1:
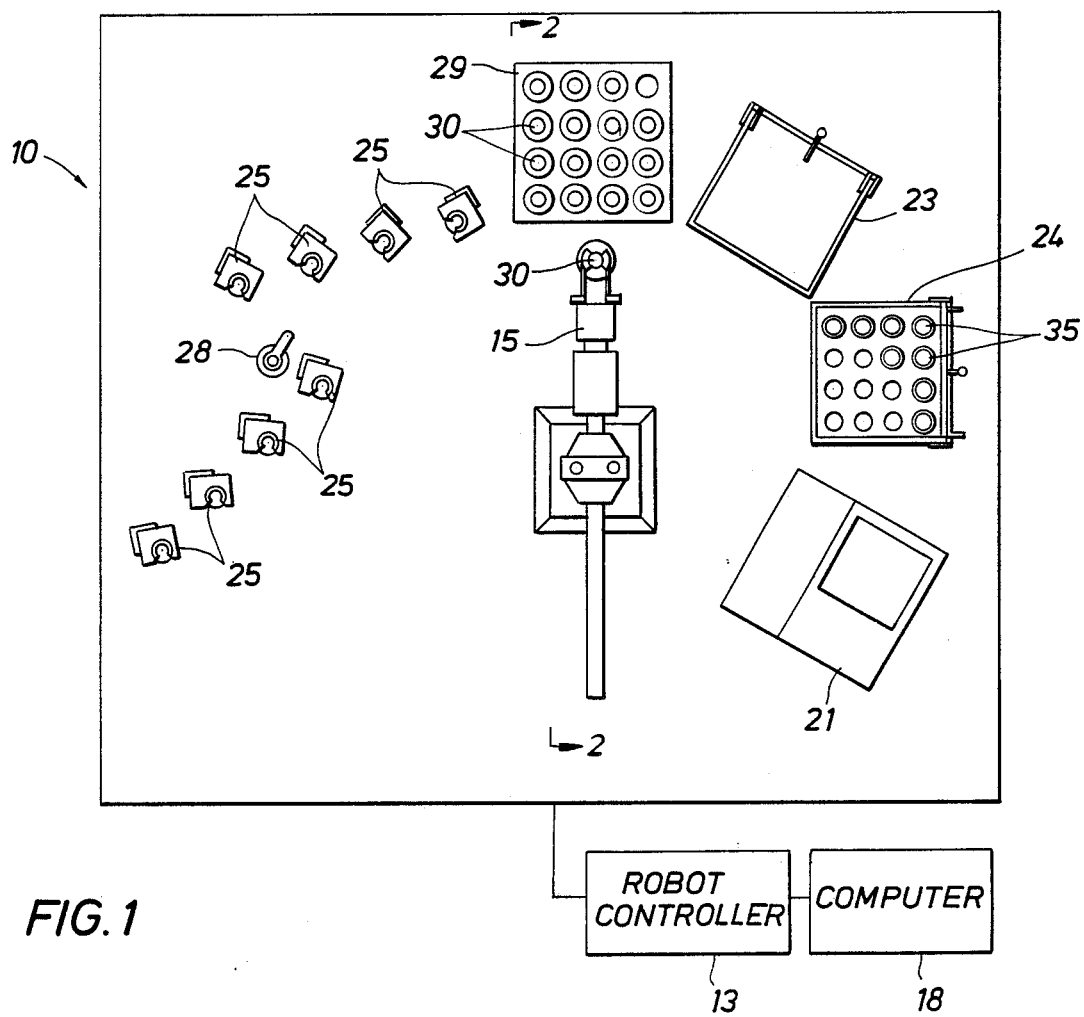
FIG. 1 is a plan view of the robotics system for automatically determining the total suspended solids in liquids.
Figure 2:
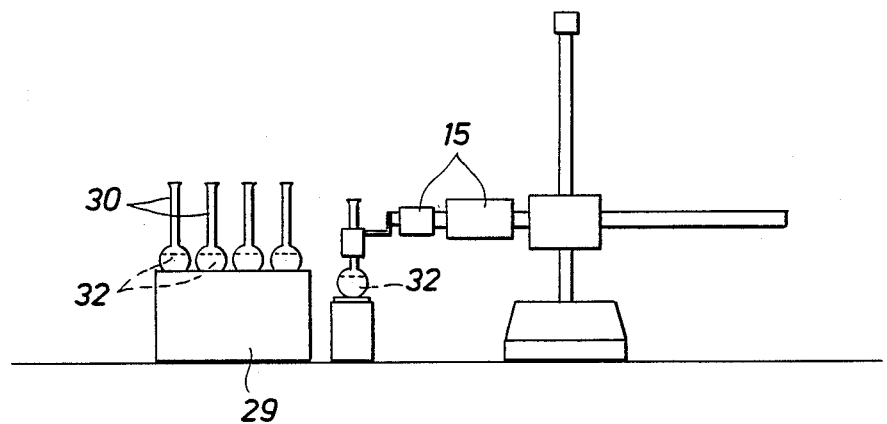
FIG. 2 is a side view of the FIG. 1 system taken on view line 2—2 in FIG. 1.

With reference to the drawings, the new and improved automated method and apparatus for determining total suspended solids in liquids will be described. FIG. 1 shows a robotics system 10 for carrying out the method according to the present invention. System 10 includes a robot controller 13 and, in the center of system 10, a robot arm and manipulator 15 controlled by controller 13. Controller 13 and arm/manipulator 15, in the preferred embodiment, are the Zymate II system available from Zymark Corporation (Hopkinton, Mass.). Suitable computer support equipment 18 may also be provided for processing, storing, printing, graphing, and other desired functions in support of the robotics system 13,15. System 10 further includes an electronic balance 21 having a remote controlled door, and an oven 23 (shown with the lid closed) and desiccator 24 (shown with the lid raised), also equipped with remote controlled doors.

Eight filtration stations 25, in the preferred embodiment, are of a special and unique design capable of detecting when filtration of the liquid has concluded, independently of the time required for the filtration. A suitable filtration station 25 and capacitance measuring configuration (FIGS. 3 and 4) is described in detail in copending U.S. patent application Ser. No. 149,254, filed contemporaneously herewith, and entitled "Liquid Sensor for Robotic Filtration Station", the disclosure of which is entirely incorporated herein by reference.

Figure 3:
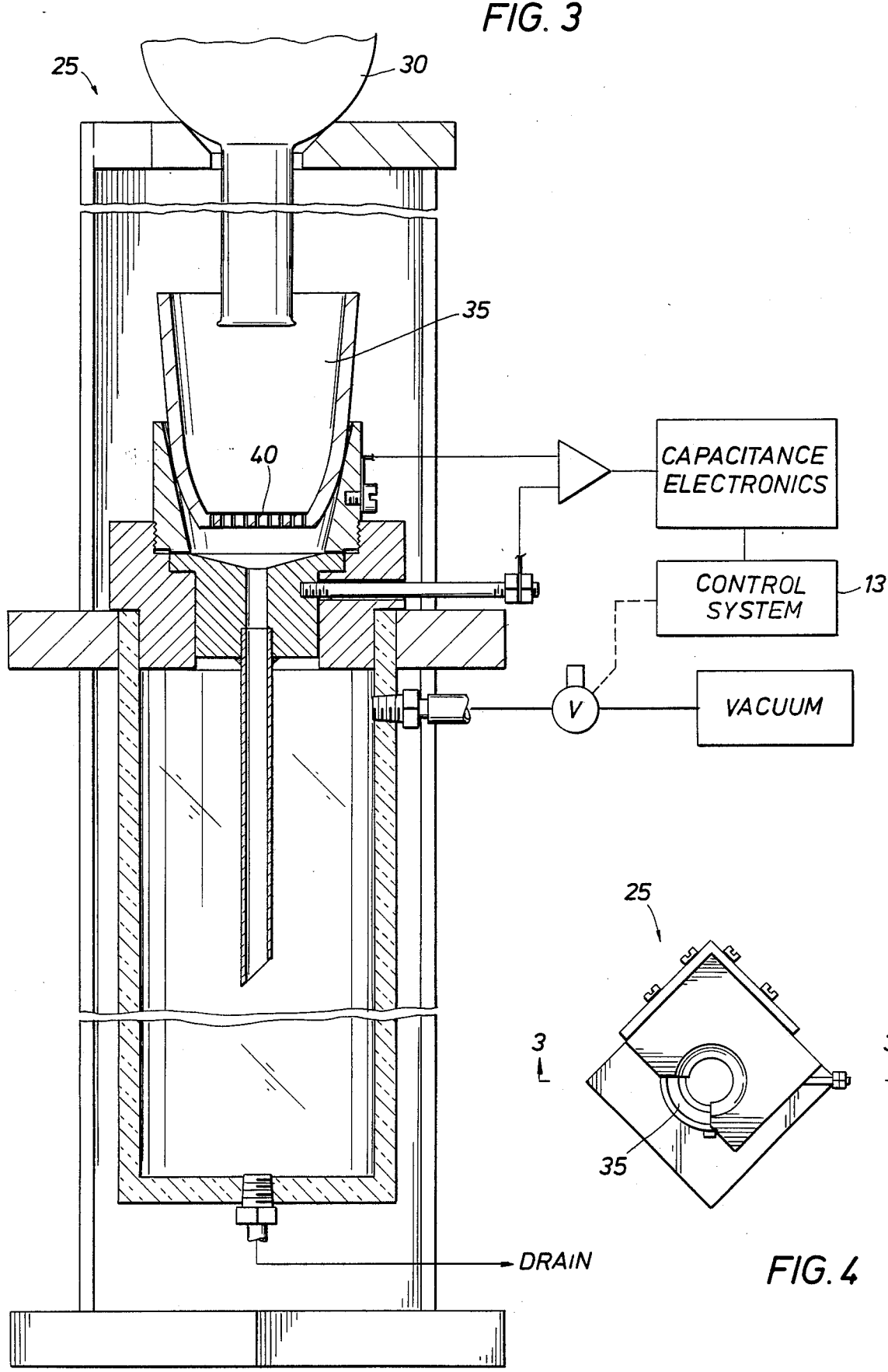
FIG. 3 is a cross-sectional view, taken generally on line 3—3 in FIG. 4, of one of the filtration stations shown in FIG. 1.
Figure 4:
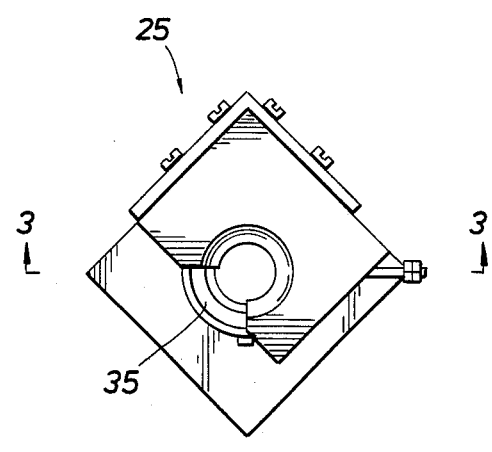
FIG. 4 is a top view of the station illustrated in FIG. 3, but with the flask omitted for clarity of illustration.
Figure 5:
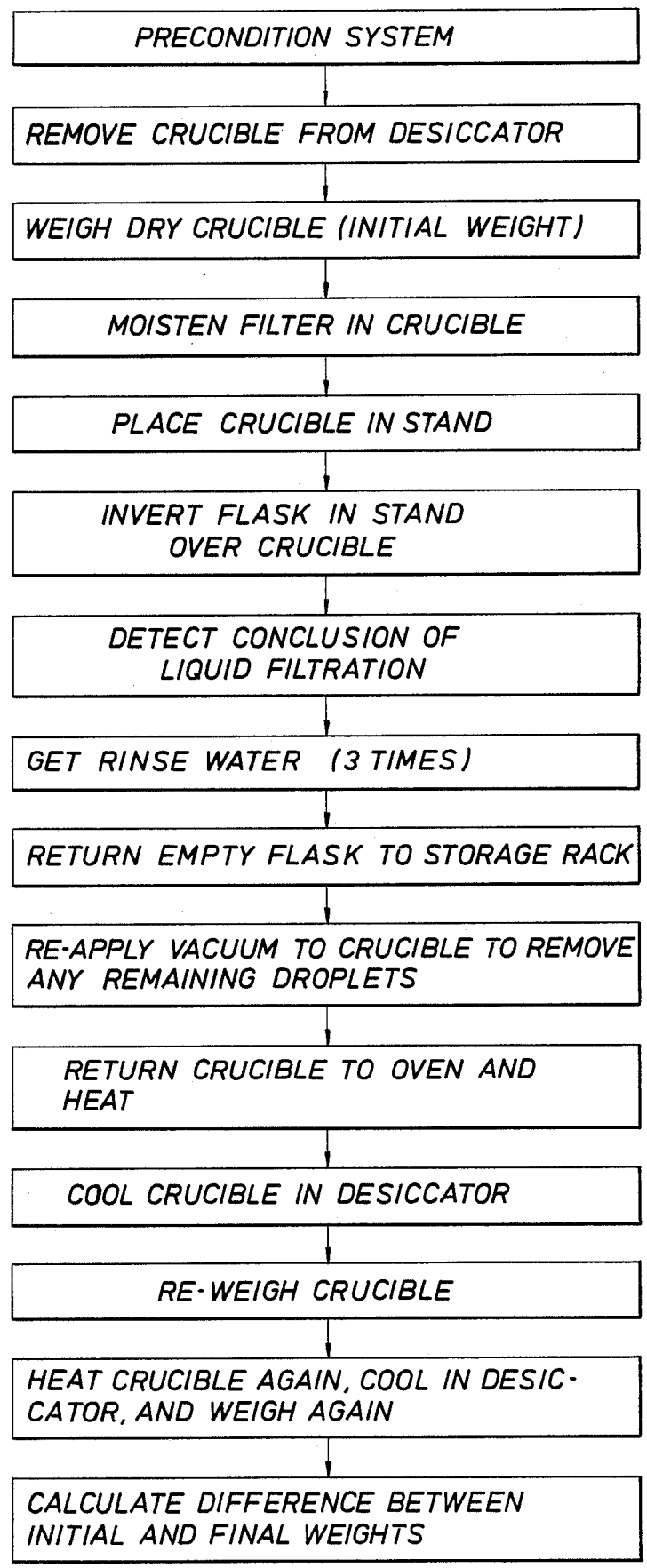
FIG. 5 is a flow chart illustrating the analytical process.

Other major components of system 10, as shown in the drawing figures, include rinse dispenser station 28 and a storage rack 29. Rack 29 is designed to hold sample-containing flasks 30 from which the liquid samples 32 therein will eventually be poured through crucibles 35 (FIG. 3) which contain filters 40 (FIG. 3).

The automated total suspended solids determination procedure then proceeds as follows. First, the operator preconditions the system. Water is loaded into the rinse dispenser station 28. The crucibles 35 with their filters 40 are heated, such as in a furnace, to drive off all organic material. The clean crucibles with clean filter are then placed (using tweezers) in the desiccator 24, and the sample-containing flasks 30 are loaded into the storage rack 29. Initial heating of the crucibles may be, for example, for fifteen minutes at 550° C., followed by cooling at ambient for thirty minutes, and then equilibration for one hour in the desiccator, before the analysis run is started. Suitable crucibles are readily available, one type being a Gooch crucible (Coors part No. 60151).

The robot 15 then removes a crucible 35 from the desiccator 24 and places it in the balance 21 to determine the initial or tare weight. Weights are automatically transmitted from the balance 21 to the memory in the robot controller 13 for subsequent calculation and results.

The robot then moves the tared crucible 35 from the balance 21 to the rinse station 28, where the filter 40 is dampened with water. The crucible is then placed in the filtration station 25.

Next, the robot 15 gets a flask 30 containing a sample 32 from the storage rack 29. Just before the robot begins to pour the sample 32 into the crucible 35, the vacuum in station 25 is applied to the bottom of the crucible 35 to assist in the filtration. Simultaneously, the capacitance sensor (not shown) in the filtration station 25 measures the base capacitance for the crucible and the dampened filter 40. The sample is then poured into the crucible and filtered. No overflow of the crucible occurs because the pouring is self regulated hydrostatically. During the filtration, the capacitance sensor in filtration station 25 repeatedly monitors the liquid level in the crucible. Filtration is finished when the capacitance reaches the original base capacitance condition. At that time the vacuum is also discontinued.

The robot 15 then moves the flask 30 from the filtration station to the rinse station 28 where rinse water is added. The flask is then moved back to filtration station 25 to pour any residual sample from the flask into the crucible 35. This also washes the filter cake which has been captured by filter 40. During this operation, the vacuum and liquid level sensing are again operated as described above.

In the preferred embodiment, the rinsing operations are repeated twice more.

The robot 15 then returns the empty flask 30 from the filtration station 25 to the storage rack 29, and then moves the crucible 35 from the filtration station to the oven 23 where the filter cake is dried at 105° C. for two hours.

After drying, the robot 15 moves the crucible 35 from the oven to the desiccator 24 for thirty minutes to cool before being weighed. The robot then moves the crucible 35 from the desiccator 24 to the balance 21 where the crucible 35, filter 40, and filter cake thereon are weighed.

To verify the final weight, the robot 15 returns the weighed crucible to the oven 23 to dry an additional fifteen minutes. After heating for this period of time, the robot then moves the crucible to the desiccator 24 where it is allowed to cool for thirty minutes before being re-weighed again. Finally, the robot moves the crucible to the balance where it is re-weighed, ordinarily verifying a constant final weight. Finally, the robot returns the crucible to the desiccator 24 where it is stored until the operator removes it at the conclusion of the measurement of all the original liquid samples 32. The difference between the initial and final weights of each individual crucible then indicate the amount of suspended solids which were captured by the respective filters 40.

If volatile total suspended solids are to be determined, in addition to just the total amount of suspended solids, then after the drying and re-weighing steps are concluded, the crucibles may be placed in a high temperature oven or furnace to vaporize the volatile suspended solids. In the preferred embodiment, this is performed at 550° C. After forty-five minutes in the furnace at this temperature, the crucibles are allowed to cool thirty minutes at ambient conditions and then returned to the desiccator for an additional sixty minutes before being re-weighed. This additional data then allows the total amount of volatile suspended solids in the filter cake to be determined as well.

As may be seen, therefore, the present invention has numerous advantages. It is extremely precise and accurate, and can be operated very successfully while unattended. Results show precisions at least as good as those with manual methods. The capital investment is modest, so that labor savings quickly justify the cost of the system. Operator time required for the procedure has been found to be less than one-third that for the manual procedure. Additionally, the invention provides advantages for the operator, who finds the robotic approach more interesting than the manual procedure and also gains additional time for performing other tasks, therefore experiencing a greater sense of productivity. The invention, in this context, is not only economical, but actually can be considered inexpensive. It is also uncomplicated, durable, very versatile, and highly reliable. It thus lends itself to wide application in automated analytical and laboratory procedures directed to the analysis of total suspended and volatile total suspended solids measurements.

Based upon the teachings herein, other improvements will suggest themselves to practitioners in this art. For example, the robot could fetch a rinse hose after the final flask rinse, and use the hose to wash down the inside of the crucible, to wash away dried solubles, such as salt, although this has not been found to be necessary.

Therefore, while the methods and forms of apparatus herein described constitute preferred embodiments of this invention, it is to be understood that the invention is not limited to these precise methods and forms of apparatus, and that changes may be made therein without departing from the scope of the invention.

What is claimed is:

1. An automated robotic method for determining total suspended solids in liquid samples wherein the liquid samples are contained in individual sample vessels, and the following steps are all executed by means of an automated robotic manipulator, comprising:
   (a) weighing a fresh, dry, filter-containing vessel to determine its initial weight;
   (b) inverting a sample-containing sample vessel over the filter-containing vessel to pour the sample into the filter-containing vessel;
   (c) detecting conclusion of the filtration of the liquid sample through the filter-containing vessel;
   (d) adding clean rinse liquid to the sample vessel;
   (e) again inverting the sample vessel over the filter-containing vessel to pour residual sample solids and rinse liquid from the sample vessel into the filter-containing vessel;
   (f) again detecting conclusion of the filtration of the liquid through the filter-containing vessel;
   (g) heating the filter-containing vessel until it is dry;
   (h) cooling the filter-containing vessel;
   (i) re-weighing the filter-containing vessel; and
   (j) calculating the difference between the initial and final weights to determine the weight of the suspended solids removed by the filter from the liquid sample.

2. The method of claim 1 further comprising storing the fresh, dry, filter-containing vessel in a desiccator prior to weighing the dry vessel to determine its initial weight.

3. The method of claim 1 further comprising moistening the filter in the filter-containing vessel prior to inverting the sample-containing vessel over the filter-containing vessel.

4. The method of claim 1 further comprising:
   (a) fetching the sample-containing sample vessel from a storage rack prior to weighing the sample-containing vessel; and
   (b) returning the empty sample vessel to the storage rack.

5. The method of claim 1 further comprising repeating the rinse steps (d), (e), and (f) at least one more time.

6. The method of claim 1 further comprising expediting filtration of the liquid sample through the filter-containing vessel by applying a vacuum thereto.

7. The method of claim 6 further comprising briefly re-applying the vacuum to the filter-containing vessel just prior to heating the filter-containing vessel in step (g).

8. The method of claim 1 further comprising, after said re-weighing step, again heating, cooling, and re-weighing the filter-containing vessel to verify the final weight.

9. The method of claim 1 further comprising:
   (a) determining volatile suspended solids by, prior to said calculating step, heating the filter-containing vessel in a furnace to vaporize the volatile suspended solids in the filtrate, cooling the filter-containing vessel, and again weighing the filter-containing vessel, substantially as before; and
   (b) based upon the weights determined in said several weighing and re-weighing steps, calculating volatile total suspended solids as well as the total of all suspended solids removed by the filter from the liquid sample.

10. An automated robotic method for determining total suspended solids in liquid samples contained in sample flasks, using a robotic system having at least a water dispensing station, a heating means, a desiccator, a storage rack for the sample-containing flasks and a filter station, said system also utilizing filter-containing crucibles, wherein the following steps except the first preconditioning step (a) are all executed by means of an automated robotic manipulator, comprising:
   (a) preconditioning the robotic system by loading clean water into the system's water dispenser, heating the filter-containing crucibles to drive off substantially all organic material, placing the filter-containing crucibles in the system's desiccator, and placing the sample-containing flasks in the storage rack;
   (b) removing a fresh, dry, filter-containing crucible from the system's desiccator;
   (c) weighing the dry crucible to determine its initial weight;
   (d) at the system's water dispensing station, moistening the filter in the crucible;
   (e) placing the crucible in the system's filtration station;
   (f) fetching a sample-containing flask from the storage rack;
   (g) inverting the sample-containing flask over the filter-containing crucible to pour the sample into the filter-containing vessel;
   (h) expediting filtration of the liquid sample through the crucible by applying a vacuum thereto;
   (i) detecting conclusion of the filtration of the liquid sample through the crucible;
   (j) filling the flask with clean rinse water at the system's water dispenser;
   (k) again inverting the flask over the crucible to pour residual sample solids and rinse water from the flask into the crucible;
   (l) again detecting conclusion of the filtration of the liquid through the crucible;
   (m) repeating the preceding three steps at least one more time;
   (n) returning the empty sample flask to the storage rack;
   (o) briefly re-applying the vacuum to the crucible just prior to heating the crucible;
   (p) heating the filter-containing crucible in an oven until the crucible and filter are dry;
   (q) cooling the crucible in the desiccator;
   (r) re-weighing the crucible;
   (s) again heating, cooling, and re-weighing the filter-containing crucible to verify the final weight; and
   (t) calculating the difference between the initial and final weights, to determine the weight of the suspended solids removed by the filter from the liquid sample.

11. The method of claim 10 further comprising:
   (a) determining volatile suspended solids by, prior to said calculating step, heating the filter-containing crucible to vaporize the volatile suspended solids in the filtrate, cooling the crucible, and again weighing the crucible, substantially as before; and
   (b) based upon the weights determined in said several weighing and re-weighing steps, calculating volatile total suspended solids as well as the total of all suspended solids removed by the filter from the liquid sample.

12. Apparatus for automated robotic determination of total suspended solids in liquid samples contained in sample vessels and using filter-containing vessels by means of an automated robotic manipulator, comprising:
   (a) means for weighing a fresh, dry, filter-containing vessel to determine its initial weight;
   (b) a filtration station;
   (c) means for placing the vessel in said filtration station;
   (d) means for inverting a sample-containing sample vessel over the filter-containing vessel to pour the sample into the filter-containing vessel;
   (e) means for detecting conclusion of the filtration of the liquid sample through the filter-containing vessel;
   (f) means for adding clean rinse liquid to the sample vessel;
   (g) means for again inverting the sample vessel over the filter-containing vessel to pour residual sample solids and rinse liquid from the sample vessel into the filter-containing vessel;
   (h) means for again detecting conclusion of the filtration of the liquid through the filter-containing vessel;
   (i) means for heating the filter-containing vessel until it is dry;
   (j) means for cooling the filter-containing vessel;
   (k) means for re-weighing the filter-containing vessel; and
   (l) means for calculating the difference between the initial and final weights to determine the weight of the suspended solids removed by the filter from the liquid sample.

13. The apparatus of claim 12 further comprising desiccator means for storing the fresh, dry, filter-containing vessels prior to weighing the dry vessels to determine their initial weight.

14. The apparatus of claim 12 further comprising means for moistening the filter in the filter-containing vessel prior to inverting the sample-containing vessel over the filter-containing vessel.

15. The apparatus of claim 12 further comprising a storage rack for the sample-containing vessels.

16. The apparatus of claim 12 further comprising means for applying a vacuum to the filter-containing vessel in the filtration station to expedite filtration of the liquid sample therethrough.

17. The apparatus of claim 16 further comprising means for briefly re-applying the vacuum to the filter-containing vessel just prior to removing the filter-containing vessel from the filtration station and heating it.

18. Apparatus for automated robotic determination of total suspended solids in liquid samples contained in storage vessels and using filter-containing crucibles by means of an automated robotic manipulator, comprising:
 (a) a water dispenser;
 (b) a desiccator;
 (c) a storage rack;
 (d) a filtration station;
 (e) means for removing a fresh, dry, filter-containing crucible from said desiccator;
 (f) means for weighing the dry crucible to determine its initial weight;
 (g) means for moistening the filter in the crucible at said water dispenser;
 (h) means for placing the crucible in said filtration station;
 (i) means for fetching a sample-containing flask from said storage rack;
 (j) means for inverting the sample-containing flask over the filter-containing crucible to pour the sample into the filter-containing crucible;
 (k) means for applying a vacuum to the crucible to expedite filtration of the liquid sample therethrough;
 (l) means for detecting conclusion of the filtration of the liquid sample through the crucible;
 (m) means for filling the flask with clean rinse water at said water dispenser;
 (n) means for again inverting the flask over the crucible to pour residual sample solids and clean rinse water from the flask into the crucible;
 (o) means for again detecting conclusion of the filtration of the liquid through the crucible;
 (p) means for returning the empty sample flask to said storage rack;
 (q) means for briefly re-applying the vacuum to the crucible just prior to heating the crucible;
 (r) means for heating the filter-containing crucible until the crucible and filter are dry;
 (s) means for cooling the crucible in said desiccator;
 (t) means for re-weighing the crucible;
 (u) means for again heating, cooling, and re-weighing the filter-containing crucible to verify the final weight; and
 (v) means for calculating the difference between the initial and final weights, to determine the weight of the suspended solids removed by the filter from the liquid sample.

* * * * *